(12) United States Patent
Avrutsky et al.

(10) Patent No.: US 12,369,799 B2
(45) Date of Patent: Jul. 29, 2025

(54) OMNIDIRECTIONAL PHOTOACOUSTIC TOMOGRAPHY SYSTEM

(71) Applicant: Wayne State University, Detroit, MI (US)

(72) Inventors: Ivan Avrutsky, Rochester Hills, MI (US); Mohammad Mehrmohammadi, Farmington Hills, MI (US)

(73) Assignee: Wayne State University, Detroit, MI (US)

( * ) Notice: Subject to any disclaimer, the term of this patent is extended or adjusted under 35 U.S.C. 154(b) by 362 days.

(21) Appl. No.: 17/971,740

(22) Filed: Oct. 24, 2022

(65) Prior Publication Data

US 2023/0046187 A1 Feb. 16, 2023

Related U.S. Application Data

(63) Continuation of application No. 16/634,634, filed as application No. PCT/US2018/043035 on Jul. 20, 2018, now abandoned.

(60) Provisional application No. 62/538,968, filed on Jul. 31, 2017.

(51) Int. Cl.
*A61B 5/00* (2006.01)

(52) U.S. Cl.
CPC .......... *A61B 5/0095* (2013.01); *A61B 5/4312* (2013.01)

(58) Field of Classification Search
CPC ................ A61B 5/0095; A61B 5/4312; A61B 2562/0233; G02B 17/061
See application file for complete search history.

(56) References Cited

U.S. PATENT DOCUMENTS

| 2,891,437 | A | * | 6/1959 | Tripp | G02B 27/32 359/729 |
| 5,878,112 | A | * | 3/1999 | Koertge | F16P 3/12 378/209 |
| 2007/0299341 | A1 | | 12/2007 | Wang | |

(Continued)

FOREIGN PATENT DOCUMENTS

WO 2013082586 A2 6/2013

OTHER PUBLICATIONS

Deng, Zijian et al., "Noninvasively Measuring Oxygen Saturation of Human Finger-Joint Vessels by Multi-Transducer Functional Photoacoustic Tomography," Journal of Biomedical Optics, Jun. 2016, pp. 061009-1 through 061009-5.

(Continued)

*Primary Examiner* — John D Li
(74) *Attorney, Agent, or Firm* — Fishman Stewart PLLC

(57) ABSTRACT

A photoacoustic tomography system includes a first ring-shaped mirror having a central axis therethrough and configured to converge light inwardly towards the central axis and a subject, and an adjustment mechanism configured to move the first ring-shaped mirror along the central axis to a plurality of different positions. Each position of the plurality of different positions allows the first ring-shaped mirror to illuminate a respective ring of light around a respective portion of the subject, and an acoustic signal detector is movable along the central axis such that acoustic signals can be detected from the respective portion of the subject when illuminated by the first ring-shaped mirror while at each respective position of the plurality of different positions.

20 Claims, 3 Drawing Sheets

(56) References Cited

U.S. PATENT DOCUMENTS

| | | | |
|---|---|---|---|
| 2013/0190595 A1 | 7/2013 | Oraevsky | |
| 2016/0058295 A1* | 3/2016 | Imai | A61B 5/0037 |
| | | | 600/407 |
| 2016/0228009 A1 | 8/2016 | Tokita | |
| 2016/0338592 A1 | 11/2016 | Masumura | |
| 2016/0345886 A1* | 12/2016 | Wang | A61B 5/0095 |
| 2017/0025149 A1 | 1/2017 | Ahner | |
| 2017/0065182 A1 | 3/2017 | Wang | |
| 2017/0103540 A1* | 4/2017 | Brokman | A61N 7/02 |
| 2017/0119345 A1* | 5/2017 | Levien | A61B 8/4461 |
| 2017/0122915 A1* | 5/2017 | Vogt | A61B 8/00 |
| 2017/0172419 A1 | 6/2017 | Oishi | |
| 2018/0010961 A1* | 1/2018 | Masumura | A61B 5/0095 |
| 2018/0303349 A1* | 10/2018 | Wang | A61B 5/0095 |

OTHER PUBLICATIONS

International Search Report dated Oct. 19, 2018 for copending Int'l Appl. No. PCT/US2018/043035.

* cited by examiner

OMNIDIRECTIONAL PHOTOACOUSTIC TOMOGRAPHY SYSTEM

CROSS-REFERENCE TO RELATED APPLICATIONS

This application is a Continuation application of and claims priority to U.S. patent application Ser. No. 16/634,634, filed Jan. 28, 2020, which is a national phase application of and claims priority to International Patent Application No. PCT/US2018/043035, filed Jul. 20, 2018, which claims the benefit of U.S. Provisional Patent Application No. 62/538,968, filed Jul. 31, 2017, the contents of each of which are hereby incorporated by reference in their entirety.

TECHNICAL FIELD

The present application relates to a system for photoacoustic tomography.

BACKGROUND

Photoacoustic tomography (optoacoustic imaging) is a biomedical imaging modality technology utilizing the photoacoustic effect. In photoacoustic tomography, non-ionizing laser pulses are delivered into biological tissues. Some of the delivered energy will be absorbed and converted into heat, leading to transient thermoelastic expansion and thus wideband (i.e. MHz) ultrasonic emission. The generated ultrasonic waves are detected by ultrasonic transducers and then analyzed to produce images. It is known that optical absorption is closely associated with physiological properties, such as hemoglobin concentration and oxygen saturation. As a result, the magnitude of the ultrasonic emission (i.e. photoacoustic signal), which is proportional to the local energy deposition, reveals physiologically specific optical absorption contrast. 2D or 3D images of the targeted areas can then be formed.

Major existing methodologies in the field of ultrasonic photoacoustic imaging, for example for scanning of breast tissue, are known as photoacoustic mammoscope, LOUISA breast imaging, and as a single-light source excitation/cup-shape acquisition photoacoustic tomography system by Optosonics Inc.

Existing photoacoustic systems not yet provide resolution and sensitivity needed for breast cancer screening. Existing technologies rely on localized illumination of breast tissue.

SUMMARY

It is an object of the present application to describe an ultrasonic photoacoustic tomography system that provides a high resolution and sensitivity without increasing the time duration of in vivo tissue examination.

This objective is achieved by an ultrasonic photoacoustic tomography system comprising a mirror arrangement configured to redirect an incoming light beam defining a central axis such that the mirror arrangement reflects the incoming light beam to form a converging ring-shaped light beam. This converging ring-shaped light beam directs light originating from the incoming light beam radially inward covering a 360° circumferential range around the central axis. A closed-geometry acoustic detector is configured to pick up reactive sound waves from tissue irradiated by the converging ring-shaped light beam over the 360° circumferential range. A closed geometry in this context may be a ring or any other geometry surrounding a central opening.

Preferably, both the converging ring-shaped light beam and the acoustic detector are configured to be movable along the central axis for scanning an object along an axial path.

In a preferred embodiment, the mirror arrangement includes at least a first mirror with a first mirror surface being cone-shaped, a second mirror being ring-shaped with a second mirror surface forming a hollow truncated cone, thus forming a light bear in the shape of a hollow cylinder, and a third mirror being ring-shaped with a third mirror surface forming a hollow truncated cone, wherein the first, second, and third mirrors are arranged coaxially with the central axis.

A mounting platform that is transparent for a wavelength bandwidth of the incoming light beam may be provided for holding the first mirror so that the propagating light is uninterrupted by any mounting structure.

The mounting platform preferably extends in a radial plane and may also hold the second mirror. In this arrangement, the mounting platform is preferably positioned between the second mirror and the third mirror.

While the mounting platform, the first mirror, and the second mirror may be in a fixed relationship relative to one another, the third mirror is preferably axially movable relative to the mounting platform, the first mirror, and the second mirror.

The closed-geometry acoustic detector may also be axially movable relative to the mounting platform, the first mirror, and the second mirror, together with or independently from the third mirror.

A drive mechanism may be provided for driving the acoustic detector and the third mirror along the central axis.

An adjustment mechanism for axially guiding the third mirror may be held by the mounting platform.

If the acoustic detector and the third mirror have a central opening with a diameter of at least 150 mm, the arrangement is suitable, for example, for breast tissue scanning.

In a further preferred embodiment, the first mirror surface has an apex configured to face the incoming light beam and to reflect the incoming light beam radially outward over the 360° circumferential range, the second mirror surface has an angle relative to the central axis configured to reflect the radially outward reflected light beam axially away from the incoming light beam, and the third mirror surface has an angle relative to the central axis configured to reflect the axially reflected light beam radially inward to form the converging ring-shaped light beam. For best detection of the photoacoustic effect, the radially inward reflected light beam encloses an angle of 30° to 80° with the incoming beam such that the illuminated area on a surface of an object to be scanned is in an axial location overlapping with an axial position of the closed-geometry acoustic detector.

The first mirror surface, the second mirror surface, and the third mirror surface are preferably first-surface mirror surfaces to prevent refractive aberrations.

An ultrasound source and ultrasound detector can be provided to determine a distance of a surface of an object to be scanned from the converging ring-shaped light beam.

With such a determination, the photoacoustic system can be configured for performing an automatic scanning procedure by adjusting a light intensity of the incoming beam based on the determined distance.

The ultrasound detector can be combined with the acoustic detector.

Further benefits of the proposed photoacoustic tomography system will become evident from the following description of preferred embodiments shown in the drawings.

The drawings are provided herewith solely for illustrative purposes and are not intended to limit the scope of the present invention.

DETAILED DESCRIPTION OF THE DRAWINGS

Figure 1:
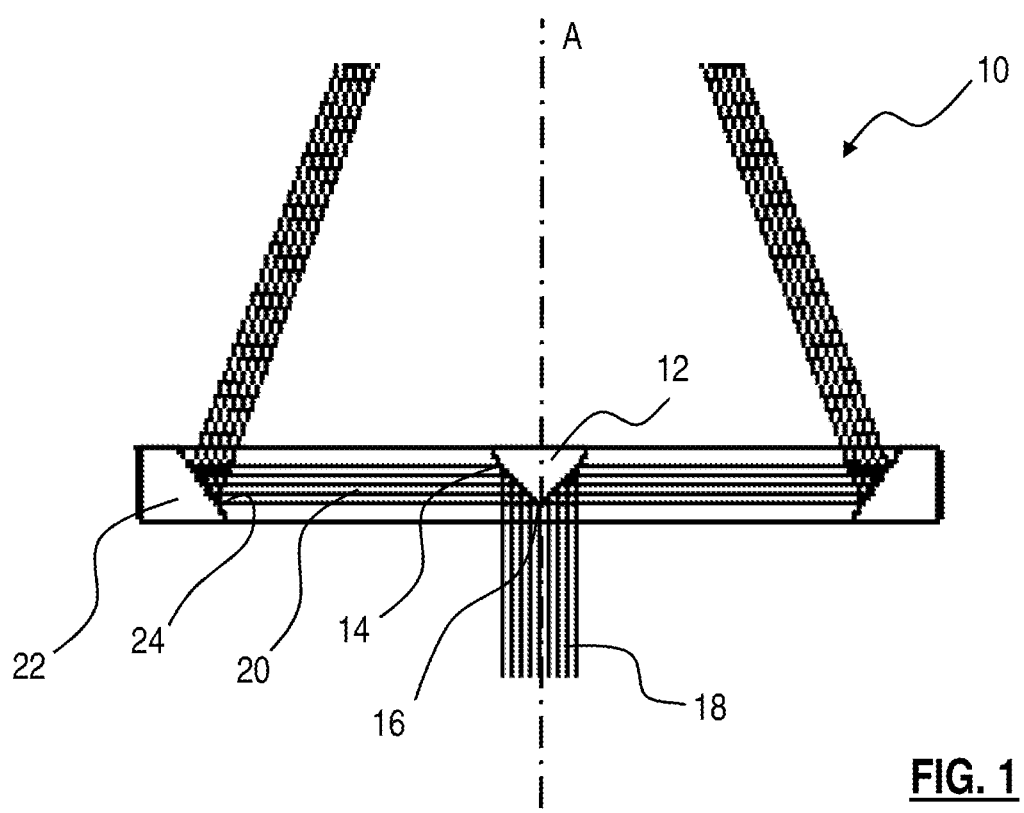
FIG. 1 shows a schematic illustration of a first mirror arrangement for an omnidirectional photoacoustic tomography arrangement.
Figure 2:
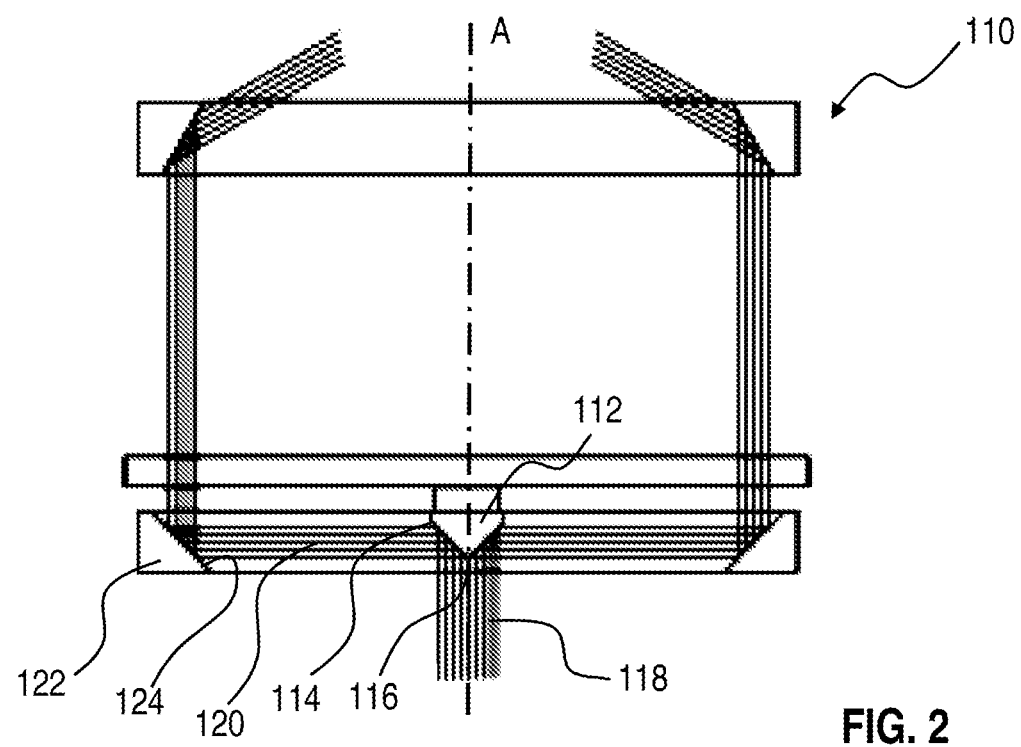
FIG. 2 shows a schematic illustration of a second mirror arrangement for an omnidirectional photoacoustic tomography arrangement.

FIGS. 1 and 2 show two schematic examples of the proposed omnidirectional photoacoustic tomography system 10 and 110, respectively. The term "omnidirectional" refers to a simultaneous ring-shaped illumination as opposed to a parallel light beam circulated around an object to be scanned.

FIG. 1 shows a simplified schematic model of a proposed omnidirectional photoacoustic tomography system 10. It comprises a first mirror 12 with a cone-shaped outer mirror surface 14 that has an apex 16 facing an incoming collimated light beam 18. The incoming light beam 18 is reflected radially outward by the cone-shaped mirror surface 14 over a complete 360° circumferential range around the central axis A defined by the collimated light beam 18. Upon the reflection by the first mirror 12, the light beam forms a generally planar light sheet 20 extending radially outward from the first mirror 12. The light intensity of the light sheet 20 decreases proportionally with the distance from the central axis A. A second mirror 22 is arranged in the path of the light sheet 20. The second mirror 22 is ring-shaped with an inner mirror surface 24 shaped like a partial hollow cone. The mirror surface 24 of the second mirror 22 has a slope relative to the central axis A that is less than 45° to create an incidence angle and a reflection angle that are both smaller than 45° to reflect the light sheet 20 radially inward for a ring-shaped illumination of any object to be scanned that is placed in a location along the central axis A. However, an axial adjustment of the ring-shaped illumination of the object would involve a movement of the object to be scanned, and an additional repositioning mechanism for the object or for the complete mirror system would be required.

Figure 3:
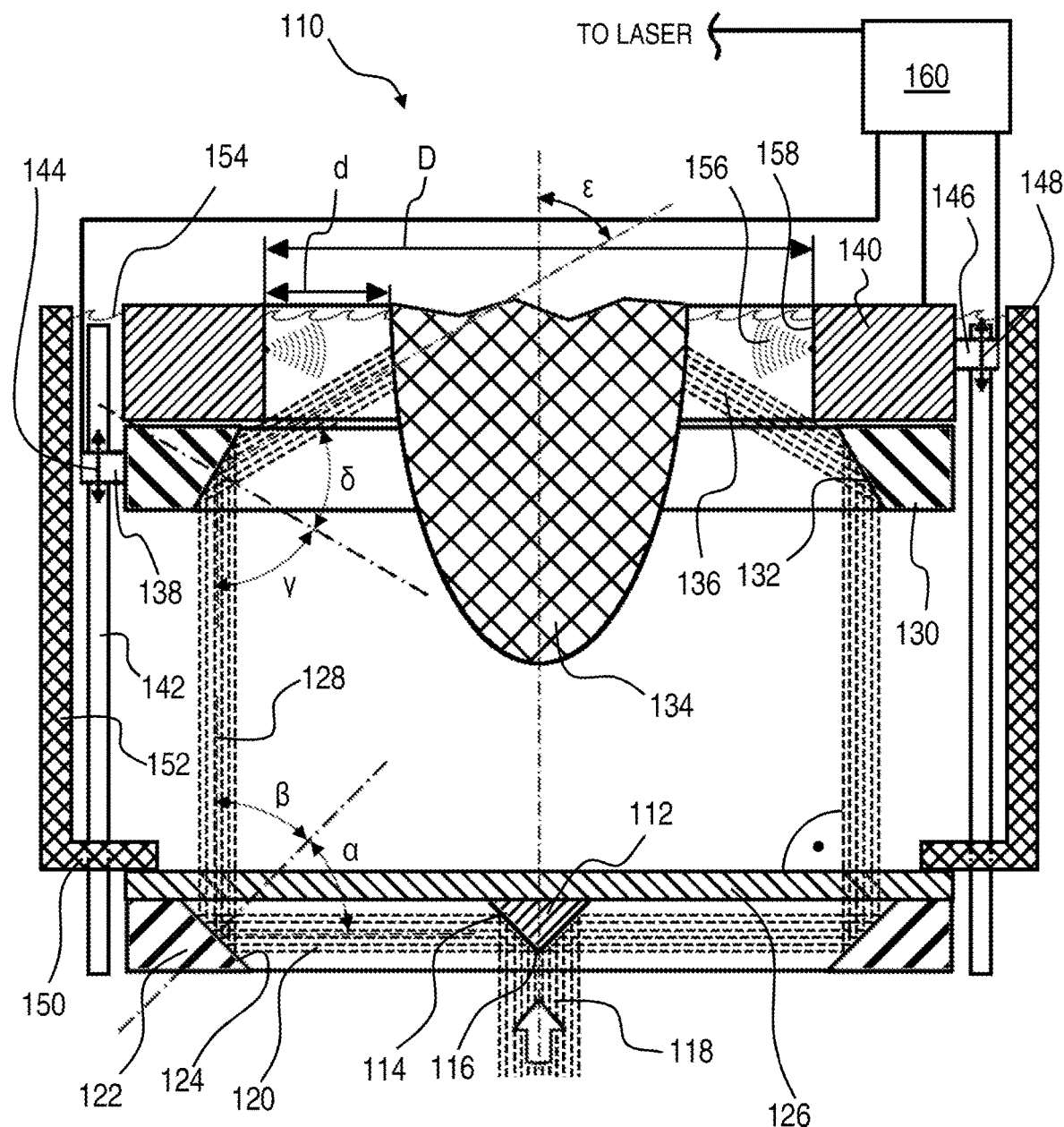
FIG. 3 shows a schematic set-up of an omnidirectional photoacoustic tomography arrangement using the second mirror arrangement.

FIG. 2 shows a second, functionally advanced, example of a proposed omnidirectional photoacoustic tomography system 110 that is also illustrated in more detail in FIG. 3. Like the example of FIG. 1, it includes a cone-shaped mirror surface 114 of a first mirror 112 that has an apex 116 facing an incoming collimated light beam 118. The incoming light beam 118 is reflected radially outward by the cone-shaped mirror surface 14 over a complete 360° circumferential range around the central axis A defined by the collimated light beam 118. Upon the reflection by the first mirror 112, the light beam 118 forms a generally planar light sheet 120 extending radially outward from the first mirror 112. A ring-shaped second mirror 122 surrounding the first mirror 112 is positioned in the path of the light sheet 120.

Both the first mirror 112 and the second mirror 122 are mounted on a transparent mounting platform 126. The material of the mounting platform 126 is chosen to be transparent to the wavelength band of the incoming collimated light beam 118 that is used to perform the photoacoustic tomography. In this context, "transparent" means that the material of the mounting platform 126 allows for a transmission of at least 50%, but preferably 90%, of the light intensity within a given wavelength band. The configuration of the mounting platform 126 (shown in FIG. 3) allows for holding the first mirror 112 in place without obstructing the light reflected by the second mirror 122. Should the incoming light beam 118 include wavelengths that are not used, the mounting platform 126 may be an optical filter that is not transparent for all wavelengths of the incoming light beam 18, but that instead may filter out (by reflection or absorption) such wavelengths that do not contribute to the excitation of a usable acoustic signal.

Because any refractive redirection of light causes chromatic aberrations, it is preferred that the incidence angle α and the reflection angle β of the second mirror 122 are identical to those of the first mirror 112, i.e. that the mirror surface 124 of the second mirror 122 is parallel to the mirror surface 114 of the first mirror 112. Thus, in the event that the light sheet 120 originating from the first mirror 112 is not entirely planar (but cone-shaped), the second mirror 122 preferably redirects the light to a direction parallel to the central axis A to form a light cylinder 128 of constant diameter. This ensures that the light cylinder 128 progresses perpendicular to the surface of the mounting platform 126 so that both the incidence angle and the refractive angle of the light passing through the mounting platform 126 are 0°.

In addition to the first mirror 112 and the second mirror 122, the photoacoustic tomography system 110 of FIG. 2 includes a third mirror 130. The third mirror is ring-shaped with a mirror surface 132 also forming a hollow truncated cone, which in this case encloses an acute angle with the central axis A and radially reflects the light cylinder 128 radially inward toward an object 134 to be scanned. As indicated in FIG. 2, the angle between the central axis A and the slope of the mirror surface of the third mirror 130 is less than 45°, for example between 15° and 40° so that the radially inward reflected light encloses a total angle ε of 30° to 80° with the incoming light beam 18, corresponding to an incidence angle γ and a reflection angle δ of 50° to 75° each. This mirror slope thus results in both the incidence angle γ and the reflection angle δ being greater than 45°. In effect, the light cylinder 128 is reflected to form a cone shape with the apex of the light cone 136 being axially farther removed from the first and second mirrors 112 and 122 than the third mirror 130. This light cone 136 is projected on the object 134 to be scanned to form an illuminated ring or sleeve extending over the entire 360° angular range around the central axis A.

The second and third mirrors 122 and 130 preferably have conical shapes. However, parabolic, spherical, or other profiles can also be used for controlling the light intensity distribution on the object 134.

The geometry of the third mirror 130 as shown has certain advantages as will become evident from the following description of FIG. 3.

In the example of FIG. 3, the angle of the first mirror surface 114 and of the second mirror surface 124 are shown at 45° to provide incidence angles and reflection angles of 45°. But as explained above, other angles are feasible as well, preferably in an arrangement, in which a light cylinder 128, which propagates parallel to the central axis A, passes through the radial mounting platform 126 at a right angle.

The third mirror 130 is axially movable via an adjustment mechanism 138 that does not require any movement of the first mirror 12 or the second mirror 122, nor a movement of the object 134 to be scanned. The shown adjustment mechanism 138 has a guiding structure 142 for axially guiding the third mirror 130 along the central axis A. Arrows indicate a drive mechanism 144 for moving the third mirror 130 via the adjustment mechanism 138.

Notably, as common in optical arrangements, all mirrors are preferably first-surface mirrors. Accordingly, all optical elements redirecting the incoming light beam 118 to form the converging ring-shaped light beam emitting the light cone 136, i.e. the first mirror 12, the second mirror 122, and the third mirror 130, are reflective and not refractive. As a result, all undesirable optical aberrations are eliminated.

Axially adjacent the third mirror 130, a closed-geometry ultrasound transducer 140 is positioned. In the shown embodiment, the ultrasound transducer 140 is ring-shaped and has its own adjustment mechanism 146 and drive mechanism 148 that may structurally resemble the drive mechanism 144 and adjustment mechanism 138 of the third mirror 130. As previously mentioned, the ultrasound transducer 140 may have a different closed geometry and may, for example, form a hollow square or another polygonal frame.

For the function of the photoacoustic tomography system 110, it may be feasible to provide only one drive mechanism 144 and one adjustment mechanism 138 for jointly moving the third mirror 130 and the ultrasound transducer 140. Where a joint drive mechanism 144 is used, the ultrasound transducer 140 may require a greater axial length of sensitivity because the illuminated ring of small-diameter objects 134 would be farther removed from the third mirror 130 than the illuminated ring of an object 134 with a large diameter. A movement of the ultrasound transducer 140 independent from the movement of the third mirror 130 as shown allows the axial position of the ultrasound transducer 140 to be adjusted relative to the third mirror 130, based on the diameter of the scanned object 134.

The photoacoustic tomography system 110 may include a water-filled container 150 with a transparent bottom formed by the mounting platform 126 and with a surrounding wall 152 sealingly secured to the mounting platform 126. The container 150 is preferably filled with water up to a water level 154 above the third mirror 130 and the enclosed ultrasound transducer 140 because air-to-glass and glass-to-water refractions will not affect the cylindrical beam formation. The guiding structure 142 is shown to be sealingly extending through the container wall 152 to the outside of the container, where it may be anchored to a supporting structure that is not shown. Alternatively, the guiding structure 142 may be mounted on the inside of the container, for example to the mounting platform 126 or to the container wall 152 so that no container openings are required.

The closed-geometry ultrasound transducer 140 preferably has a dual function. On the one hand, it detects the acoustic signals caused in an object 134 by the light cone 136. On the other hand, the ultrasound transducer 140 performs the sonic determination of the distance d between the object 134 and the ultrasonic transducer 140. For the sonic determination, ultrasound waves 156 are emitted radially inward from the closed-geometry ultrasound transducer 140. The acoustic detector in the ultrasound transducer 140 receives the reflected ultrasound waves and determines the distance d of the object 134 in a manner known per se.

The distance information is then fed to a scanning algorithm that not only determines the axial length, along which the scanning process is performed, but also the light intensity required for uniform illumination at different axial positions, and further the required relative axial positions of the ultrasound transducer 140 and the third mirror 130 with respect to each other. The intensity adjustment takes into account that, in a converging light wave such as the light cone 136, the intensity increases closer to the center of convergence and can partly compensate for light attenuation due to absorption or scattering losses.

For example, the sonic determination may be performed in a first scanning process, followed by the photoacoustic tomography scanning process that is calibrated based on the parameters acquired during the first scanning process. Alternatively, a single axial movement may alternate between the sonic determination of the distance d and the photoacoustic tomography scanning process in quick succession. Of course, the ultrasound transducer 140 may be a separate element from the acoustic detector for the photoacoustic tomography system 110 without leaving the scope of the present invention.

It is further contemplated that the photoacoustic tomography system 110 of FIG. 3 is arranged in the orientation as shown, which means that the central opening 158 of the ultrasound transducer 140 forms an upper insertion opening for the object 134 to the scanned and that the incoming light beam 118 originates from below the shown structure. This has the benefit that gravity will promote a proper arrangement of the object 134 along the central axis A without requiring additional support structures inside the photoacoustic tomography system 110. If the photoacoustic tomography system 110 is to be used for breast scanning, the central opening 148 of the ultrasound transducer 140 and of the third mirror 130 is preferably dimensioned to be large enough to insert a human breast for breast cancer scanning. Thus, for a breast scanner, the opening should have a diameter D of at least 150 mm.

The light source used for the photoacoustic tomography scanning process is chosen based on the material of the object 134 to be scanned. The wavelengths for photoacoustic tomography are typically within the visible and near infrared spectrum for body tissue, but may be within a different spectral range for different materials of the object 134 to be scanned. Thus, the proposed photoacoustic tomography system 110 may be a modular addition to an existing photoacoustic tomography system that includes a feasible light source for a given purpose, or the photoacoustic tomography system 110 may be built as a stand-alone unit including one or more lasers suited for the intended application or applications.

The proposed photoacoustic tomography system 110 ensures a fully enclosed light path that does not require any shielding from environmental noise, be it electromagnetic or acoustic waves. As the lasers used for photoacoustic tomography scanning are pulsed, any background noise can be measured between pulses and be subtracted from the yielded acoustic signal. This allows for easy access to the space between the second mirror 122 and the third mirror 130 for proper positioning of the object 134 prior to the scanning process.

Accordingly, the present application provides a novel illumination system for enhanced photoacoustic tomography with all-reflective, aberration-independent, adjustable optics for generating a ring-shaped illumination pattern on an object to be scanned.

The described full-ring illumination and detection provides a platform for fast, optimized photoacoustic tomography with enhanced penetration depth without the need for painful tissue compression. By simultaneously scanning entire rings or slices of tissue, the scanning process is greatly accelerated compared to existing photoacoustic tomography systems. The closed geometry of the acoustic transducer elements allows for a more efficient acquisition of the omnidirectional photoacoustic signals.

Prototype

A small-scale prototype to confirm the feasibility of omnidirectional illumination has been assembled and tested using off-the-shelf parabolic reflectors in lieu of conical ring mirrors. To initially test the effect of ring illumination, preliminary photoacoustic studies were conducted. Due to the small-size of the prototype optics (50 mm ring diameter) and limitations of integrating the small size prototype with actual ring acoustic detection, the experiments were designed as follows: a converging cylindrical shape illumination was generated by adjusting the distance between the first mirror and the second mirror. A cone-shape tissue-mimicking phantom, made out of 10% porcine gelatin (300 bloom) and 50 µm cellulose particles, was added to create "light scattering" as well as an "acoustic backscattered" medium. An optical absorber (700 µm pencil lead) was embedded within the phantom and oriented diagonally so that light absorbing points would be distributed at different distances from the outer surface of the phantom. The converging ring illumination, combined with a geometry of the phantom, simulated the generation of a ring on a cylindrical breast shape. A programmable US scanner (Verasonics Vantage 128), equipped with a linear array transducer (L11-4v) was utilized to acquire US and photoacoustic signals along the diameter of the phantom.

Figure 4:
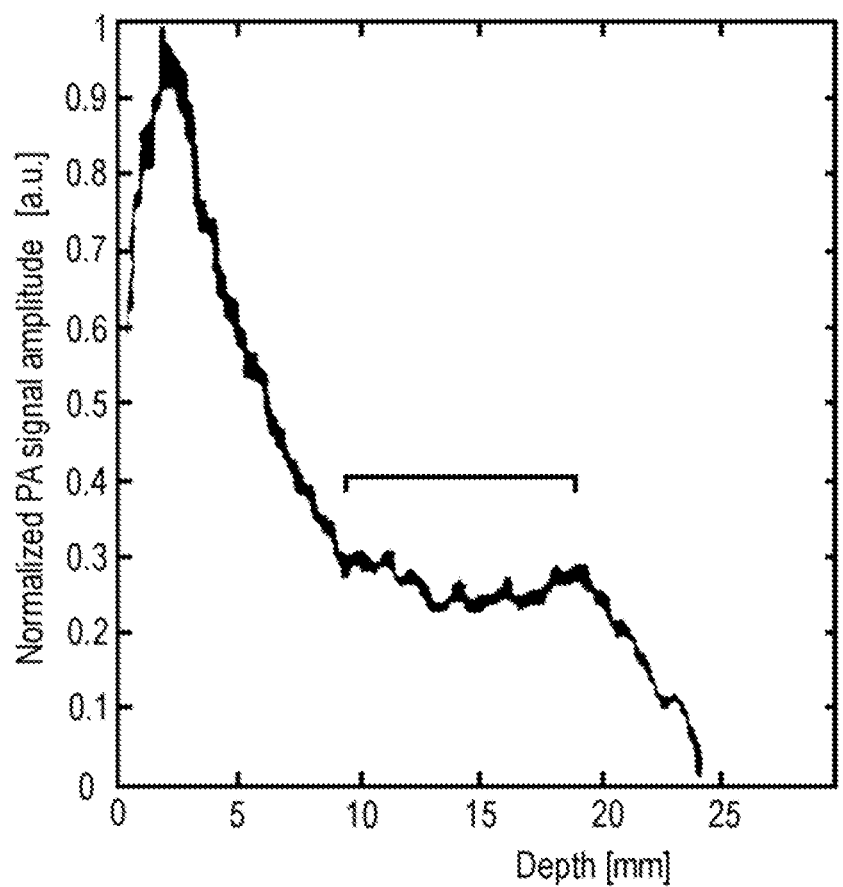
FIG. 4 is a graph of a test scan of simulated tissue performed with a set-up similar to that of FIG. 3.

The sliced illumination generated by ring illumination and medium diffusion is shown in the graph of FIG. 4. In the graph, the photoacoustic signal intensity is plotted (in arbitrary units with the maximum signal set to "1") across the diameter of the phantom (i.e. distance from the outer surface of the phantom in mm). The laser energy was set to be 10 mJ/pulse (at 532 nm).

As anticipated, the photoacoustic signal intensity is elevated just below the surface layer due to the high density of photons. However, the normalized photoacoustic amplitude clearly shows that passing the high-fluence superficial layer, the photoacoustic signal remained quite uniform over a range of distances between 10 and 22 mm, indicating that omnidirectional ring illumination generated a relatively uniform light energy deposition with respect to depth. The photoacoustic signal vanished after 25 mm because the diagonal placement of the pencil lead placed it outside of the illuminated region. This also demonstrated that with ring illumination, it is possible to focus the laser energy within a specific slice of the tissue instead of illuminating the whole object.

Advantages

The proposed UST/PAT system is different and advantageous compared to existing technologies. For example, compared to a PA mammoscope as developed by the University of Twente in cooperation with Canon Inc., the presented system does not require breast compression. The main issue with mammographic photoacoustic configurations, in addition to the discomfort, is that breast compression causes the blood to rush out, which adversely affects photoacoustic performance. Blood is the major endogenous photoacoustic contrast medium and biomarker. Compared to LOUISA 3D breast imaging developed by Tomowave or a photoacoustic tomography system by Optosonics, which utilizes a single-light-source excitation and a cup-shaped acquisition, the presented method is expected to have an improved penetration depth and a more uniform illumination pattern. This assumption is based on preliminary in-silico Monte Carlo simulation and on the above described tissue mimicking phantom study using a prototype.

Table 1 below provides a comparative overview:

TABLE 1

Comparison between proposed UST/PAT and competing technologies

| | Imaging hemoglobin related biomarkers | Imaging modalities/image representation | SOS, AA, and Fluence compensation ability | Breast Coverage (areas close to chest wall) |
|---|---|---|---|---|
| Proposed system | Yes | 3D US, PA, Elasticity | Yes | Yes |
| PA Mammoscope | Not efficient | 2D PA | No | Yes |
| LOUISA 3D system | Yes | 2D US, 3D PA | No | Yes |
| Optisonics System | Yes | 3D PA | No | No |

In addition, accurate ultrasound tomography imaging via the ultrasound transducer, including speed-of-sound maps and acoustic-attenuation maps may be used prior to the photoacoustic tomography performed by the system described above for a precise measurement of the acoustic heterogeneity of the breast tissue. The preceding ultrasonic measurements provide information for implementing advanced reconstruction algorithms to compensate for acoustic heterogeneity of the breast tissue that may be indicative of non-uniform light fluence. Such advanced and model-based reconstruction methods significantly enhance the quality of photoacoustic tomography in terms of sensitivity and resolution and, more importantly, enables quantitative photoacoustic imaging.

While the above description constitutes the preferred embodiments of the present invention, it will be appreciated that the invention is susceptible to modification, variation and change without departing from the proper scope and fair meaning of the accompanying claims.

The invention claimed is:

1. A photoacoustic tomography system comprising:
   a first ring-shaped mirror having a central axis through an opening of the first ring-shaped mirror, the first ring-shaped mirror configured to converge light inwardly towards the central axis;

an adjustment mechanism configured to move the first ring-shaped mirror along the central axis such that the first ring-shaped mirror may be i) moved to a first position to direct a first ring of light around a first circumference of a first portion of a subject ii) moved to a second position to direct a second ring of light around a second circumference of a second portion of the subject and iii) moved to a third position to direct a third ring of light around a third circumference of a third portion of the subject; and a distance detector to enable a determination of i) a first distance between the first portion and the distance detector when at the first position, ii) a second distance between the second portion and the distance detector when at the second position, and 3) a third distance between the third portion and the distance detector when at the third position, wherein the photoacoustic tomography system is configured to adjust light intensity when the first ring-shaped mirror is at each of the first, second, and third positions based on the respective first, second, and third distances.

2. The photoacoustic tomography system of claim 1 wherein the distance detector is movable along the central axis to different distance detector positions to enable the photoacoustic tomography system to determine the first distance, the second distance, and the third distance.

3. The photoacoustic tomography system of claim 2 further comprising an acoustic detector movable along the central axis to different acoustic detector positions to enable the acoustic detector to detect acoustic signals from i) the first portion when illuminated by the first ring of light, ii) the second portion when illuminated by the second ring of light, and iii) the third portion when illuminated by the third ring of light.

4. The photoacoustic tomography system of claim 3 wherein the acoustic detector and the distance detector are a ring-shaped ultrasound transducer such that the ring-shaped ultrasound transducer detects the acoustic signals and enables distance determinations.

5. The photoacoustic tomography system of claim 4 further comprising a container configured to hold water such that at least a portion of the first ring-shaped mirror, the ring-shaped ultrasound transducer, and at least one of the first, second, and third portions are under the water during operation.

6. The photoacoustic tomography system of claim 2 further comprising:
a cone-shaped mirror configured to receive collimated light incoming along the central axis and reflect the collimated light radially outward; and
a second ring-shaped mirror configured to receive the radially outward reflected light and reflect it into a cylindrical wall of light that impinges on the first ring-shaped mirror.

7. The photoacoustic tomography system of claim 6 further comprising a mounting platform having a top side and a bottom side, wherein the cone-shaped mirror and the second ring-shaped mirror are coupled to the bottom side of the platform and the first ring-shaped mirror is above the top side of the mounting platform.

8. The photoacoustic tomography system of claim 7 wherein the second ring-shaped mirror is configured to direct the cylindrical wall of light perpendicularly through at least the bottom side of the mounting platform, and wherein an inner reflective surface of the first ring-shaped mirror is substantially parallel to an inner reflective surface of the second ring-shaped mirror.

9. The photoacoustic tomography system of claim 7 wherein the mounting platform is transparent to the cylindrical wall of light, and wherein the mounting platform filters out undesirable light.

10. A photoacoustic tomography system comprising:
a first ring-shaped mirror having a central axis therethrough and configured to converge light inwardly towards the central axis and an object along the central axis;
an adjustment mechanism configured to move the first ring-shaped mirror along the central axis to a plurality of positions along the central axis, wherein each position of the plurality of positions allows the first ring-shaped mirror to illuminate a respective ring of light around a respective portion of the object, and wherein each respective portion of the object is at a different position along the central axis; and
an acoustic signal detector movable along the central axis such that acoustic signals can be detected from the respective portion of the object when illuminated by the first ring-shaped mirror.

11. The photoacoustic tomography system of claim 10 further comprising a distance detector that enables the photoacoustic tomography system to determine a distance between the distance detector and the respective portion of the object illuminated by the first ring-shaped mirror while at each respective position of the plurality of positions.

12. The photoacoustic tomography system of claim 11 wherein the acoustic signal detector and the distance detector are a ring-shaped ultrasound transducer such that the ring-shaped ultrasound transducer at least detects the acoustic signals and enables distance determinations, wherein the object is part of a subject.

13. The photoacoustic tomography system of claim 11 wherein the photoacoustic tomography system is configured to adjust a light intensity of light incoming to the first ring-shaped mirror based on the distance such that the light intensity of the light incoming to the first ring-shaped mirror increases as the distance decreases and the light intensity of the light incoming to the first ring-shaped mirror decreases as the distance increases.

14. The photoacoustic tomography system of claim 13 wherein the distance detector is movable along the central axis such that the distance detector can be moved to a plurality of detector positions to enable each determination of the distance.

15. The photoacoustic tomography system of claim 10 further comprising:
a mirror configured to receive collimated light incoming along the central axis and reflect the collimated light radially outward; and
a second ring-shaped mirror configured to receive the radially outward reflected light and reflect it towards the first ring-shaped mirror.

16. The photoacoustic tomography system of claim 15 wherein the mirror is a cone-shaped mirror and the radially outward reflected light is a planar sheet of light around the central axis, and wherein an inner surface of the first ring-shaped mirror is substantially parallel to an inner surface of the second ring-shaped mirror.

17. The photoacoustic tomography system of claim 16 further comprising a mounting platform having a top side and a bottom side, wherein the cone-shaped mirror and the second ring-shaped mirror are coupled to the bottom side of the platform and the first ring-shaped mirror is above the top side of the mounting platform.

18. The photoacoustic tomography system of claim 17 wherein the second ring-shaped mirror is configured to reflect incoming light perpendicularly through at least the bottom side of the mounting platform.

19. The photoacoustic tomography system of claim 17 wherein the mounting platform is transparent to the light reflected from the second ring-shaped mirror towards the first ring-shaped mirror, and wherein the mounting platform filters out undesirable light.

20. The photoacoustic tomography system of claim 17 further comprising a container configured to hold water such that the first ring-shaped mirror is at least partially submerged water during operation, wherein the mounting platform comprises a bottom of the container.

* * * * *